United States Patent [19]

Fulton, Jr.

[11] 4,189,501
[45] Feb. 19, 1980

[54] COMPOSITION AND METHOD FOR THE TREATMENT OF ACNE

[75] Inventor: James E. Fulton, Jr., Key Biscayne, Fla.

[73] Assignee: A. H. C. Pharmacal, Inc., Miami, Fla.

[21] Appl. No.: 840,339

[22] Filed: Oct. 7, 1977

[51] Int. Cl.$^2$ .................. A61K 31/075; C11D 9/50
[52] U.S. Cl. ........................... 424/338; 252/96; 252/107; 424/358
[58] Field of Search .................. 424/338, 358; 252/107, 252/96

[56] References Cited

U.S. PATENT DOCUMENTS 3,535,422  10/1970  Cox et al. ........................... 424/164
4,056,611  11/1977  Young ................................. 424/338

OTHER PUBLICATIONS

Handbook of Non-Presription Drugs, 5th Ed., 1/77, pp. 317–323.

*Primary Examiner*—Leonard Schenkman
*Attorney, Agent, or Firm*—Blum, Kaplan, Friedman, Silberman & Beran

[57] ABSTRACT

Compositions containing organic peroxides are effective for the treatment of acne. Decomposition of the organic peroxide during storage is prevented by the incorporation of glycerol which is sufficiently effective so that decomposition is prevented even in those peroxides which are so unstable as to be explosive.

18 Claims, 3 Drawing Figures

STABILITY OF BENZOYL PEROXIDE IN SOLVENT VEHICLES AT 45°C

▲ GLYCEROL
△ DISTILLED WATER
● BRIJ 30
○ PROPYLENE GLYCOL
■ ETHANOL

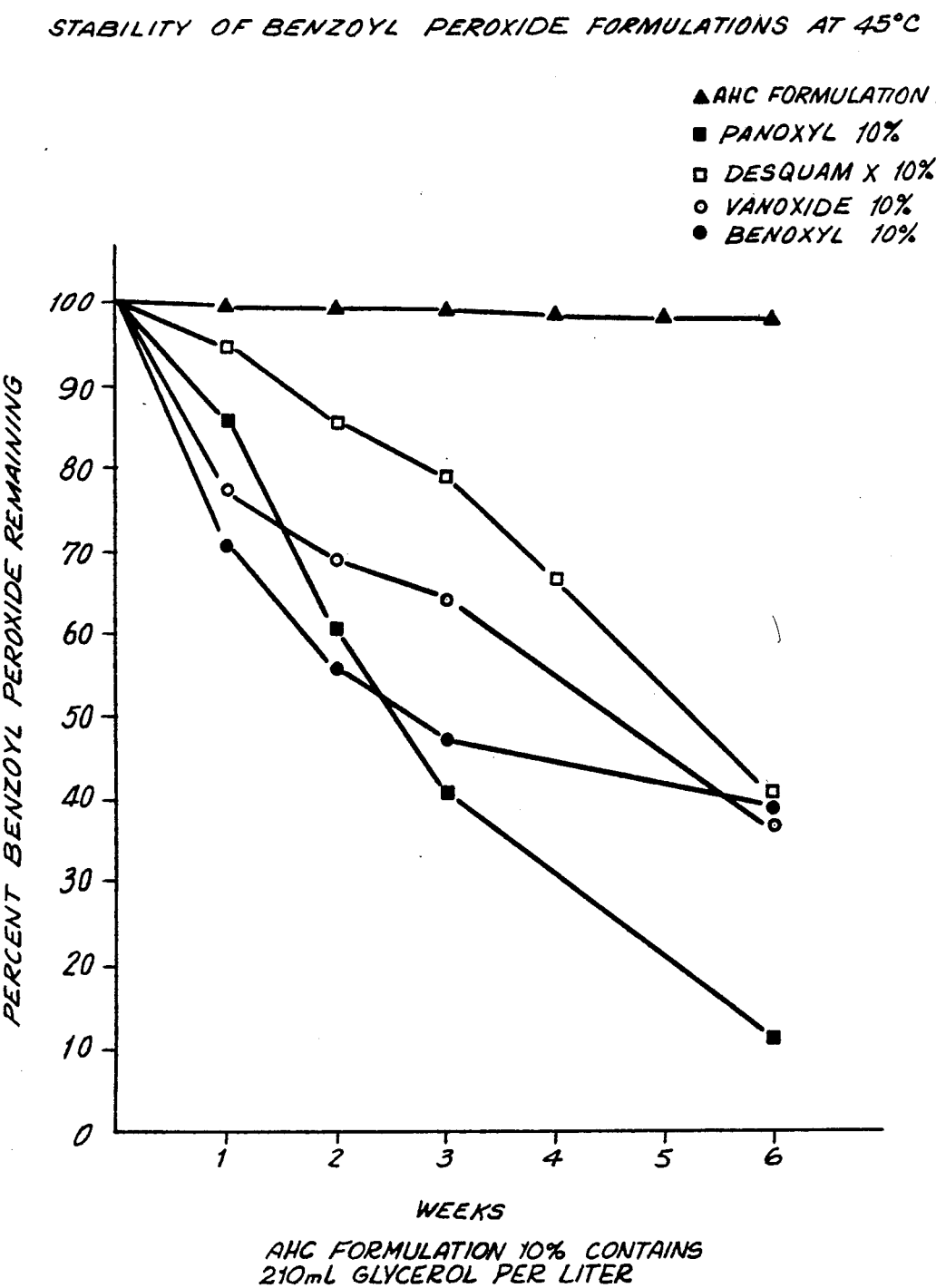

COMPOSITION AND METHOD FOR THE TREATMENT OF ACNE

BACKGROUND OF THE INVENTION

Acne vulgaris affects virtually all youngsters beginning at the age of about 13 years and continuing through the age of 23 years. In females the onset may occur at an age as early as 10 or later on in the 20's or 30's. As is evident from all of the media, this affliction is sufficiently frequent and the mental suffering, particularly, sufficiently severe so that many companies vie for the resultant market for appropriate medications. The number of anti-acne products sold over the counter and by prescription is enormous.

Many compounds and compositions have been tested and prescribed for the disease and a number have been fairly effective, but, as yet, there has been no complete cure for acne.

Therapy is extremely important since if acne is left untreated, cysts form which result in permanent pitting and disfiguring scarring. Moreover, since acne is a disease primarily of adolescence, when the sufferers are most uncertain of themselves in their new roles, the attendant stigma, both supposed and real, can be the source of severe psychological trauma.

There appears to be no doubt but that the increased flow of hormones at the onset of and during adolescence is the primary etiologic agent, since these hormones increase the size of the sebaceous glands and increase the secretion produced by these glands. However, no correlation has been found between the amount of endogenous serum hormone levels and the severity of acne in the individual.

The sebaceous glands which are present in the dermal layer of the skin produce sebum. These glands are concentrated particularly on the face, upper torso including both the chest and back, and on the scalp. Susceptibility to acne is usually greatest on the nose and on the face.

As the sebum is produced it normally flows slowly onto the surface of the skin. When the ducts through which the sebum flows are blocked, the sebum cannot reach the surface of the skin so that pressure builds up in the ducts and the ductal wall ruptures, allowing the sebum to seep into the skin's dermal layers, causing inflammation. Applying pressure to the inflamed area spreads the sebum into the dermal tissue and spreads the inflammation over a wider area.

The sebum is broken down by microorganisms which are normally present in and on the skin, the principal microorganism being C. acnes. This microorganism produces lipase enzymes which hydrolyze the triglycerides of the sebum, forming the free fatty acids which are responsible for the externally visible comedones. The plug formed when a sebaceous duct is blocked is called a "comedo". The comedo itself is a noninflammatory lesion consisting of lipid and keratin. The lesions may initiate as papules which in turn may evolve into pustules. However, the lesions may also be in the form of deeper nodules which enlarge into cysts.

Diet was originally considered to be one of the principal factors responsible for acne, the other being a lack of complete cleanliness. Chocolate was frequently considered the major villain, but recent studies have shown that neither strict prohibition of suspected foods nor strict hygienic cleansing of the skin gives the desired elimination of acne.

With the recognition of the fact that bacteria were responsible, treatment with antibiotics became popular, tetracycline being the drug of choice. However, the degree of improvement produced by the use of any of the antibiotics was so small that it was frequently unrecognizable. Treatment with sulphur lotions has a long history but, again, this material by itself failed to produce substantial improvement of the condition.

Complicating this situation has been the fact that young women, particularly, resort to the use of cosmetics, many of which, despite claims to the contrary, proved to be severely comedogenic. Increase in the severity of the acne caused by cosmetics then leads to the use of similar materials as covering agents, further exacerbating the condition.

A. M. Kligman in work carried out in cooperation with James E. Fulton, Jr. discovered that peeling of the skin induced by topical application of Vitamin A acid, also called retinoic acid was beneficial in the treatment of acne, and U.S. Pat. No. 3,729,568 issued to Kligman in 1973. Approximately simultaneously, the effect of topical application of benzoyl peroxide was also investigated and it was found that the treatment was relatively effective. U.S. Pat. No. 3,535,422 entitled "Stable Benzoyl Peroxide Composition" issued to Richard M. Cox and Leonard R. Clufo in 1970.

The effectiveness of benzoyl peroxide in the treatment of acne proved to be a function of the stability of the composition applied to the affected region. Cox et al taught that dispersing benzoyl peroxide in a fluid medium consisting only of water and organic emollients produced a substantially inert, stable composition. This stability is necessary if the product is to have a reasonable shelf-life, either in the pharmacy or in the family medicine chest. However, as will be shown below, benzoyl peroxide compositions prepared in accordance with any of the formulations heretofore available decompose rapidly during storage. Decomposition of the benzoyl peroxide when in contact with the skin is desirable since it is the oxidizing effect of the free radicals produced on decomposition which provides the desired effect. However, decomposition during storage severely reduces the effectiveness of a composition which is prepared so that it has initially the optimum concentration.

As is evident, then, a composition in which the benzoyl peroxide is stable during storage and yet decomposes readily on contact with the skin would be highly desirable, as would be a method of treatment based on such a composition. Moreover, other organic peroxides have also been found to be effective for the treatment of acne and some of these are even more unstable during storage than is benzoyl peroxide. It would also be desirable that a means of contributing stability of such peroxides during storage be provided.

SUMMARY OF THE INVENTION

A medium for the dispersion of organic peroxides contains glycerol as an inhibitor against the decomposition of such peroxides during storage between the time of dispersing the peroxide in the medium to form a composition and the time of use of said composition. For certain uses it is also desirable that a gelling agent be included in the composition, the preferred form of the composition being a soft gel or grease. The viscosity of the composition should be such that it can be applied with the finger to form a thin film on the skin which can readily be wiped off after remaining in contact with the skin for a prescribed period. The preferred gelling agent is Carbopol 940, a carboxyvinyl polymer having a molecular weight of about 4,000,000 manufactured by B. F. Goodrich Company said resin being highly ionic and slightly acidic and soluble. When this gelling agent is used the pH of the composition should be adjusted with alkali to about 4. Compositions containing a peroxide and glycerol as the stabilizer may also take the form of lotions or soaps, such compositions being useful as surgical scrubs.

The content of organic peroxide in the composition may range from 10 to 300 grams per liter of composition. The preferred range of concentrations, the preference being based on effectiveness, is from about 100 grams to 200 grams per liter of composition. The glycerol content may range from 50 to 500 ml per liter. With the glycerol may be combined up to 200 grams of propylene glycol per liter.

Sulphur may also be incorporated with advantage in the organic peroxide composition, the quantity of sulphur used being from 10 to 300 grams per liter of composition.

A preferred method of treatment is the application of the composition to the affected area once per day with the removal of the composition from the skin when a feeling of irritation is noted. Application of retinoic acid to the skin between applications of the organic peroxide composition may also prove advantageous in certain cases.

Certain of the peroxides are so unstable that they can be stored and shipped only under refrigeration. Dispersing of these peroxides in glycerol yields a composition in which the peroxide is sufficiently stable so that the composition can be shipped.

Accordingly, an object of the present invention is a composition suitable for the treatment of acne of all grades of severity, the composition containing an organic peroxide and an inhibitor against decomposition of said peroxide, said composition being useable as such or modifiable to form a lotion or a soap effective for surgical scrub.

A further object of the present invention is a composition suitable for the treatment of acne, said composition including an organic peroxide, an inhibitor against the decomposition of the peroxide and sulphur.

A significant object of the present invention is a highly effective method of treating acne.

An important object of the present invention is a method of preparing a composition for the treatment of acne where the composition includes an organic peroxide and an inhibitor for stabilizing said organic peroxide.

Still another object of the present invention is a composition including an organic peroxide and an inhibitor against decomposition of said peroxide, wherein said composition is sufficiently stable to permit shipment of same.

Still other objects and advantages of the invention will in part be obvious and will in part be apparent from the specification.

The invention accordingly comprises the composition possessing the features, properties and the relation of constituents which are exemplified in the following detailed disclosure, the several steps and the relation of one or more of such steps with respect to each of the others in the manufacture of said composition, and the several steps and the relation of one or more of such steps with respect to each of the others in the method of use of said composition, all of which are exemplified in the following detailed disclosure, and the scope of the invention will be indicated in the claims.

BRIEF DESCRIPTION OF THE DRAWINGS

For a fuller understanding of the invention, reference is had to the following description taken in connection with the accompanying drawings, in which:

FIG. 3 is a graph showing the stability of various commercial benzoyl peroxide formulations at 45° C., the stability of said commercial formulations being compared with a formulation in accordance with the present invention.

DESCRIPTION OF THE PREFERRED EMBODIMENTS

Benzoyl peroxide, used for the treatment of acne, was originally viewed as a skin irritant causing peeling in much the same way as does retinoic acid. However, I have found that when areas affected with acne are treated in accordance with the present invention both the count of C. acnes and free fatty acid in the sebum are reduced. Since it is the bacteria which are responsible for the production of free fatty acid it is evident that benzoyl peroxide as well as other organic peroxides, both alkyl and acyl, when applied as taught herein, reduce the severity of or eliminate once by sterilization of the pores.

The analysis of sebum was carried out in accordance with the procedure described in the paper entitled "Sebum: Analysis by Infrared Spectroscopy" by Arthur S. Anderson and James E. Fulton and published in the Journal of Investigative Dermatology Vol. 60, No. 3 pages 115–120.

Figure 1:
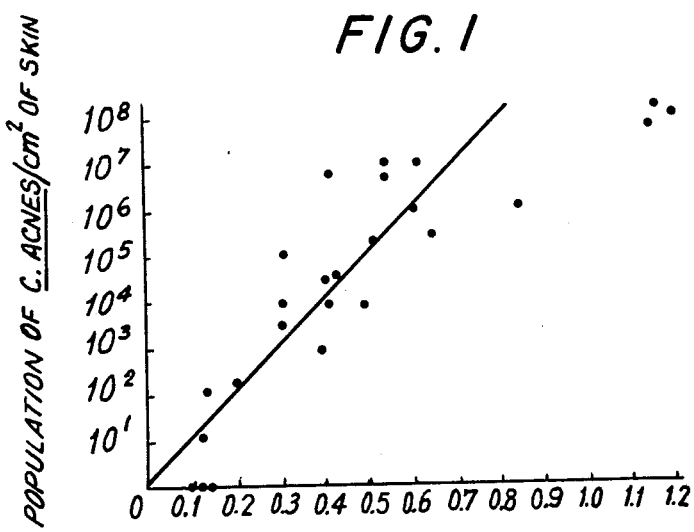
FIG. 1 is a graph of the concentration of C. acnes of the skin as a function of the fraction of free fatty acid in fatty esters in the sebum.

FIG. 1 shows the relationship between the content of free fatty acid in sebum and the concentration of C. acnes in skin. This Figure is taken from the paper entitled "Studies on the Mechanism of Action of Topical Benzoyl Peroxide and Vitamin A Acid in Acne Vulgaris" by James E. Fulton, Jr., A FarzadBakshandeh and Sara Bradley and published in the Journal of Cutaneous Pathology 1974, volume 1, pages 191–200. The abcissa in FIG. 1 is actually the rate of production of C. acnes per square centimeter of skin and the ordinate is the ratio of free fatty acid, FFA to fatty esters in the sebum, FE. Since C. acnes is primarily responsible for the lesions on the skin, it can be seen that the ratio FFA/FE correlates directly with the concentration of C. acnes of the skin. Further, since topical application of benzoyl peroxide and other organic peroxides quickly reduces the concentration of the bacteria, it is therefore evident that the organic peroxides function in the alleviation and cure of acne by sterilization of the skin.

I have found that compositions prepared as described below are effective in the alleviation and cure of acne.

A vehicle is prepared which contains an inhibitor against the decomposition of organic peroxide, the inhibitor being glycerol. For the preparation of one liter of a composition including dispersed organic peroxide, the quantities of ingredients in the vehicle are 50 to 500 ml of inhibitor, 0 to 200 ml of propylene glycol, 1,2-propanediol being the preferred propylene glycol, and water in an amount needed to bring the total quantity of the composition up to one liter.

The base to be combined with the above vehicle to prepare a liter of dispersion of organic peroxide may contain from 10 to 300 grams of organic peroxide, preferably benzoyl peroxide.

Preferably, the dispersion is thickened to the consistency of a soft gel or grease. Appropriate thickeners are finely divided silica, also known as "Fumed Silica", magnesium aluminum silicate and Carbopol 940, manufactured by B. F. Goodrich. Carbopol 940 is a carboxyvinyl polymer having a molecular weight of about 4,000,000. The base should also contain sufficient alkali to bring the pH of the composition to a value between 3.5 and 5.0, the range from 3.5 to 4.0 being preferred. Where benzoyl peroxide is used as the organic peroxide, this is added in the form of pellets, the commercial preparation containing 78% benzoyl peroxide and 22% water. Following is a sample composition which may be regarded as the basic composition from which others are prepared by adjustment of the quantities and nature of ingredients.

|  |  |  | Concentration Range |
|---|---|---|---|
| I. VEHICLE: | H₂O | 600 ml. | q.s. |
|  | Glycerol | 200 ml. | 50–500 |
|  | Propylene Glycol (1,2-propanediol) | 50 ml. | 0–200 |
|  |  | 850 ml. |  |
| II. BASE: | 78% Benzoyl Peroxide | 128 gm. | 1–30% |
|  | Carbopol 940 | 7 gm. | .5–2% |
|  | 1N NaOH | 5 gm. | 1 ml to 20 ml |
|  | Makes | 1 liter. |  |

The benzoyl peroxide is added to 600 ml of the vehicle in a high-shear blender, and agitated for several minutes until dispersion is complete and the product is uniform. The Carbopol 940 is dissolved in 200 ml of the vehicle and this solution is then added to the benzoyl peroxide dispersion. Agitation is continued until the lotion is smooth, after which the NaOH in the form of a 1N solution is added, blending being continued until the resultant soft gel is homogenous. The gel can be packaged in plastic tubing, or in resin-lined aluminum tubing. Due to its acidic nature it cannot be packaged in unlined metallic tubing.

As will be evident, the quantities given above can be increased and batches of any desired size can be manufactured according to the procedure described.

Additional ingredients may also be incorporated in the composition. Sulphur, particularly, has been found advantageous in certain cases. The quantity of sulphur added may be up to about 300 grams per liter of dispersion, about 10 grams per liter being the minimum effective quantity. Iron oxide, or other pigments may be added to give color to the composition. Alternatively, a composition may be prepared similar to that given above except for the content of organic peroxide. Instead, iron oxide or other pigment is added to give a desired color. Such a composition is termed a "cover-up". It may be used in combination with the peroxide composition to disguise the presence of the peroxide composition on the skin. The advantage of the composition combining stabilized peroxide with colorant is that it serves as a cosmetic which can be kept on the skin throughout the day, the peroxide content being adjusted to correspond to the tolerance of the patient.

Figure 2:
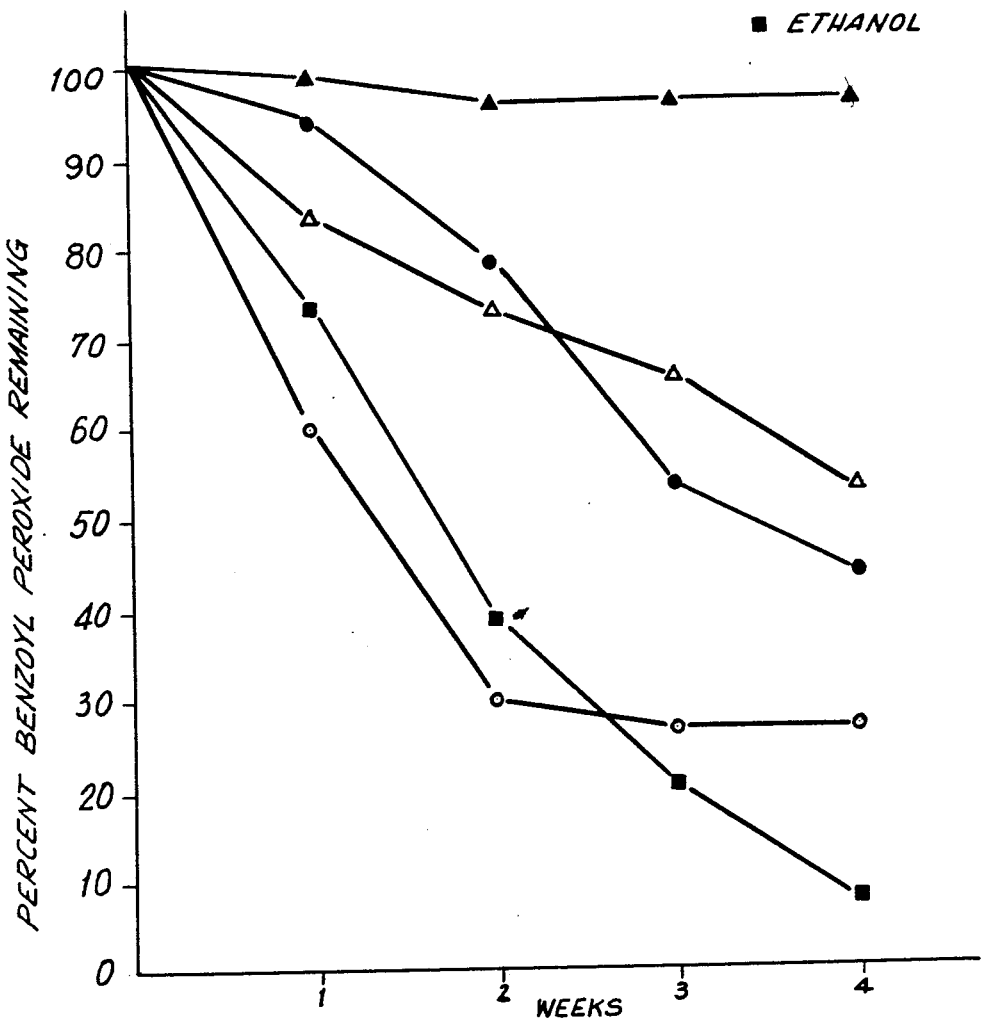
FIG. 2 is a graph showing the stability of benzoyl peroxide in various solvent vehicles at 45° C.

It is believed that the action of the glycerol is to reduce the solubility of the peroxide in the vehicle. As a result of the fact that the solubility of the peroxide is reduced, the rate of decomposition of the peroxide in the composition during storage is greatly decreased. Studies have been carried out comparing the rates of decomposition of benzoyl peroxide in various solvents. The results are shown in FIG. 2, the tests having been carried out at 45° C. to accelerate the decomposition. As can be seen at the end of 4 weeks, virtually all of the benzoyl peroxide in a composition within the scope of the present invention and manufactured by AHC Pharmaceutical Inc. remains intact. In contrast, only about 7% of the benzoyl peroxide remains after this period of time when the benzoyl peroxide is mixed with ethanol. Propylene glycol alone, as the solvent, decomposes the benzoyl peroxide even more rapidly for the first two weeks, after which the decomposition substantially stops, about 27% of the original benzoyl peroxide remaining. The rate of decomposition is substantially slower in water, about 52% of the benzoyl peroxide remaining after 4 weeks at 45° C. Brij 30, referred to in FIG. 2, is the trade-name for polyoxyethylene-4-lauryl ether.

Since the organic peroxide appears to be of limited solubility in the vehicle taught herein, the resultant composition may be referred to as a "dispersion". However, it is to be recognized that the invention is not limited to the mechanism proposed herein or by the terminology used, since some of the organic peroxide is undoubtedly soluble in the vehicle. The use of the term "dispersion" is followed because of convenience and is not intended to indicate the state of the organic peroxide in the vehicle.

That the combination of an organic peroxide with an inhibitor such as glycerol has practical effectiveness from the standpoint of stability can be seen from FIG. 3 which provides the results of storage tests at 45° C. carried out on a number of commercial formulations all of which initially have 10% of benzoyl peroxide therein. Compared with these commercial preparations is a formulation prepared in accordance with the present invention, and indicated as AHC Formulation 10. As can be seen from FIG. 3, all of the commercial preparations show serious losses of active benzoyl peroxide after 6 weeks of storage at 45° C. whereas the composition containing 10% of benzoyl peroxide and formulated in accordance with the present invention retains about 98% of the initial benzoyl peroxide after the 6 weeks storage period.

A substantial number of organic peroxides are presently available, a particularly desirable organic peroxide being the succinyl peroxide. Succinic acid, while somewhat less effective than benzoyl peroxide in the treatment of acne, has a major advantge in that the small percentage of individuals who are allergic to benzoyl peroxide are not similarly allergic to succinic acid. The reason that benzoyl peroxide may be allergenic is that the benzoyl radical formed in a hapten, haptens being substances which attach to a protein molecule and form an antigen. However, succinic acid is a normal constituent of the body in various biochemical processes and specifically in those concerned with the production of energy. Consequently, the succinic acid radical which is formed is not a hapten and thus the danger of sensitization or allergenic reaction is completely avoided. Lauryl and cumyl peroxides have also been found to be effective though not as effective as benzoyl peroxide.

Surfactants can be included in stabilized benzoyl peroxide compositions without impairing the stability thereof. Following is a composition which is a lotion, effective as a surgical scrub, and which is a modification of the basic composition presented above.

| LOTION | |
|---|---|
| Distilled Water | 550 ml |
| Glycerol | 200 ml |
| Propylene glycol | 100 ml |
| Benzoyl Peroxide (78%) | 32 gm |
| Carbopol 940 | 15 gm |
| Stepanol | 40 gm |
| Sodium Lauryl Sulfate | 40 gm |
| Sodium Hydroxide 3 N | 20 gm |

Note: Stepanol is a sodium alkyl sulfate manufactured by Stepan Corp. of Illinois.

The benzoyl peroxide content in the above lotion formulation is 2.5%. As is evident, the concentration of peroxide and of the other components can be varied, as can the peroxide used, in ways apparent to those skilled in the art.

Benzoyl peroxide, stabilized with glycerol may also be added to a conventional soap to provide benefits similar to those which accrue from the use of the compositions already taught. More particularly, a soap containing up to about 10% of a peroxide and containing glycerol in a ratio to the content of said peroxide similar to the ratios in the compositions taught above is an effective surgical scrub. Benzoyl peroxide is the preferred peroxide because of its relatively low cost and high effectiveness. Where compounds which may react with an organic peroxide are present in the soap stock to be combined with peroxide and glycerol, such compounds should be removed as by conventional means prior to formulation.

A formulation suitable for a surgical scrub soap contains about 1% to about 20% by weight of an organic peroxide, preferably benzoyl peroxide and sufficient glycerol to stabilize the peroxide. Propylene glycol may be incorporated in the soap if desired, as may conventional soap builders.

The number of gelling agents which can be used is substantial, virtually any water-soluble polymer of sufficiently high molecular weight being appropriate. Carboxymethyl cellulose has been tested and found to be quite effective. Magnesium aluminum silicate and fine silica as previously noted can also gel the solution. However, the quantity of fumed silica necessary to obtain the same increase in viscosity provided by a given quantity of Carbopol 940 is about 10 times as great.

Therapy with benzoyl peroxide is preferably commenced slowly; for example the dispersion should be allowed to remain on the skin or 3 to 4 hours daily. The initial burning sensation subsides rapidly after the first few weeks and exposure time can be increased. Where the patient is sufficiently sensitive so that irritation is excessive to the point where it may be termed "toxic", the condition is rapidly reversible within a day or two after interruption of treatment. Therapy can then re-commence. Over 3-4 weeks, the skin becomes hardened and accommodated to the treatment. As the patient becomes more accustomed to the use of the peroxide, the concentration and frequency of application may be gradually increased to the level required to maintain control. Although concentrations as high as 30% in benzoyl peroxide and 30% in sulphur may be utilized, the maximum concentration is preferably 20% for benzoyl peroxide and 10% for sulphur. Tests have shown that the addition of sulphur in this concentration to benzoyl peroxide definitely increases the efficacy of the composition.

In clinical studies, improvement is readily ascertained from the dramatic change in the total lesion count. In carrying out tests and evaluating the results of same, the lesions are graded by arbitrary standards from grades I through IV with grade IV being the most severe.

TABLE I

TOTAL LESION COUNT AT TWO WEEK INTERVALS DURING TREATMENT FIRST CLINICAL STUDY

| Group & Medication | Initial Visit | 2 Week Visit | 4 Week Visit | 6 Week Visit | 8 Week Visit |
|---|---|---|---|---|---|
| Acne, Grade I & II | 25.3 | 15.5* | 15.0* | 9.2 | 8.8 |
| Benzoyl Peroxide 10% | (22) | (22) | (16) | (5) | (9) |
| | 21.3 | 10.5* | 9.1* | 15.2 | 9.0 |
| | (20) | (20) | (10) | (6) | (2) |
| Acne, Grade III & IV | 38.7 | 23.5* | 17.8* | 14.9* | 14.1* |
| Benzoyl Peroxide 20% + Sulfur 10% | (180) | (180) | (133) | (78) | (60) |

* = p<0.05
() = number of patients in each group

Table I shows the results of a clinical study in which patients with acne of grades I and II were treated with a gel (dispersion) containing 10% benzoyl peroxide and patients with grades III and IV acne were treated with a gel (dispersion) containing 20% of benzoyl peroxide and 10% of sulphur. As is evident, the number of lesions decreased substantially during the 8-week period for the groups of patients. In fact, for the patients with acne of grades I and II, the benzoyl peroxide at a level of 10% produced significant improvement within 2 weeks, the improvement progressing to a controlled condition at the end of the period. A significant marked decrease was also demonstrated for the group having grades III and IV acne which was treated with 20% benzoyl peroxide and 10% sulphur dispersion.

In a second clinical study utilizing a more confined population similar results were obtained with a gel containing 10% benzoyl peroxide and 5% sulphur. The results are summarized in Table II.

TABLE II

TOTAL LESION COUNT AT TWO WEEK INTERVALS DURING TREATMENT SECOND CLINICAL STUDY

| Group & Medication | Initial Visit | 2 Week Visit | 4 Week Visit | 6 Week Visit | 8 Week Visit |
|---|---|---|---|---|---|
| Acne, Grade I & II 10% Benzoyl Peroxide | 27.4 (48) | 18.9* (48) | 18.0* (29) | 17.5* (17) | 16.3* (11) |
| Benzoyl Peroxide 10% + Sulfur 5% | 31.8 (28) | 24.6* (28) | 28.4* (19) | 19.8* (10) | 8.0 (5) |
| Acne, Grade III & IV Benzoyl Peroxide 20% + Sulfur 10% | 28.2 (50) | 18.8* (50) | 12.9* (28) | 12.8* (19) | 8.4* (14) |

* = p<0.05
() = number of patients in each group.

In general, treatment with a gel containing 20% of benzoyl peroxide and 10% of sulphur shows the most consistent and dramatic reduction in lesion count.

The treatment with organic peroxide dispersion can be supplemented with treatment with retinoic acid. Thus, if the organic peroxide gel is applied in the morning, then retinoic acid may be applied in the evening.

The retinoic acid is preferably used at a concentration of about 0.001% to 0.01% in a non-irritating vehicle. It should not be formulated in ethanolic solutions which are irritating to the skin when used in conjunction with a material which tends to remove layers of the skin. A suitable vehicle for the Vitamin A acid is a low-boiling ester such as ethyl acetate or a ketone such as acetone. An excellent response which is considered synergistic is to apply the retinoic acid solution to the skin and allow it to dry for about 10 minutes, after which benzoyl peroxide gel is applied directly over the Vitamin A acid.

A number of the organic peroxides are known which are sufficiently unstable so that they must be refrigerated. Others are so unstable that they may explode. Obviously, both of these types of compounds present difficulties with respect to shipment and use. I have found that dispersion of these organic peroxides in glycerol solution renders these compounds sufficiently stable so that they may be shipped without refrigeration and without presenting the danger of explosion.

A particular advantage of the compositions described herein for the treatment of acne and of the treatment mode described is that the course of treatment requires the presence of a physician only intermittently. In general, a nurse can readily be trained to discern the progress of the treatment and whether a condition has arisen which requires the skill of a physician. Consequently, the extended treatment involved in alleviation of acne is made substantially less expensive than would be the case were it necessary for each application of the medicament to be made under the observation of a physician.

It will thus be seen that the objects set forth above, among those made apparent from the preceding description, are efficiently attained, and, since certain changes may be made in carrying out the method of manufacturing the various products and in the compositions set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. A composition, comprising a dispersion of about 10 weight % of benzoyl peroxide in an aqueous solution containing about 20 volume % glycerol to inhibit decomposition of said peroxide, said composition being effective in the treatment of acne.

2. The composition as claimed in claim 1, further comprising sufficient gelling agent to increase the viscosity thereof to that of a grease.

3. The composition as claimed in claim 1, wherein said composition further contains 5 to 100 grams of gelling agent per liter.

4. The composition as claimed in claim 3, wherein said gelling agent is selected from the group consisting of carboxymethyl cellulose, magnesium aluminum silicate, finely-divided silica and carboxyvinyl copolymer.

5. The composition as claimed in claim 1, in combination with sufficient alkali to bring the pH of said dispersion to between about 3.5 and 5.0.

6. The composition as claimed in claim 1, wherein said gelling agent is carboxyvinyl copolymer in a concentration range of 5 to 20 grams per liter of said composition.

7. The composition as claimed in claim 1, further comprising from 10 to 300 grams of finely-divided sulphur per liter of same.

8. The composition as claimed in claim 1, further comprising an effective amount of a surfactant compound.

9. The composition as claimed in claim 1, further comprising a coloring amount of a pigment.

10. A method of treatment of acne, comprising the step of applying topically to an affected area a composition comprising an aqueous dispersion of an organic peroxide effective in the treatment of acne, each liter of said composition comprising about 100 grams of benzoyl peroxide, about 200 ml of glycerol, from 0–200 ml of propylene glycol and water, said step being repeated until a desired decrease in severity of said acne is achieved.

11. The method as defined in claim 10, wherein each liter of said composition further comprises 5 to 100 grams of gelling agent.

12. The method as defined in claim 11, wherein said gelling agent is a member selected from the group consisting of carboxymethyl cellulose, magnesium aluminum silicate, finely-divided silica and carboxyvinyl copolymer.

13. The method as defined in claim 11, wherein said gelling agent is carboxyvinyl copolymer in an amount of 5 to 20 grams per liter of said composition.

14. The method as defined in claim 10, wherein each liter of said composition contains alkali in an amount such that the pH of said composition lies between about 3.5 and 5.0.

15. The method as defined in claim 10, wherein each liter of said dispersion further includes 10–300 grams of finely-divided sulphur.

16. The method as defined in claim 15, further comprising the step of applying retinoic acid to said affected area at a time of day when said affected area is essentially free of said dispersion.

17. The method as defined in claim 10, wherein said dispersion is applied daily and allowed to remain on said affected area for a period up to about 6 hours, said period being commensurate with the resistance of the skin to irritation by said dispersion, and comprising the step of removal of said dispersion.

18. A surgical scrub soap, comprising about 10 weight % of benzoyl peroxide, and about 20 volume % of glycerol to stabilize said peroxide, said soap being free of ingredients reactive with said benzoyl peroxide.

* * * * *